United States Patent [19]
Takeda et al.

[11] Patent Number: 5,537,880
[45] Date of Patent: Jul. 23, 1996

[54] AUTOMATIC PIPETTING APPARATUS WITH LEAK DETECTION AND METHOD OF DETECTING A LEAK

[75] Inventors: Masaaki Takeda; Yuko Kato, both of Mitaka, Japan; Brent A. Pelletier, Mundelein, Ill.

[73] Assignee: Abbott Laboratories, Abbott Park, Ill.

[21] Appl. No.: 481,677

[22] Filed: Jun. 7, 1995

[51] Int. Cl.$^6$ .......................... G01N 35/10; G01M 3/26
[52] U.S. Cl. .................... 73/864.25; 73/864.14; 73/863.01; 73/40
[58] Field of Search .......................... 73/864.24, 864.25, 73/864.14, 863.01, 863.02, 863.03, 40, 40.5 R, 46, 49.1

[56] References Cited

U.S. PATENT DOCUMENTS

| | | |
|---|---|---|
| 3,283,565 | 11/1966 | Müller et al. . |
| 3,754,434 | 8/1973 | Guild . |
| 3,766,785 | 10/1973 | Smernoff . |
| 3,933,048 | 1/1976 | Scordato . |
| 3,935,734 | 2/1976 | Keegan . |
| 4,061,037 | 12/1977 | Keegan . |
| 4,083,363 | 4/1978 | Philpot, Jr. ................ 73/54.07 |
| 4,117,727 | 10/1978 | Friswell et al. .............. 73/864.21 X |
| 4,187,724 | 2/1980 | Citrin . |
| 4,369,665 | 1/1983 | Citrin ........................ 73/864.18 |
| 4,478,094 | 10/1984 | Salomaa et al. ............. 73/863.32 |
| 4,555,957 | 12/1985 | Frankel et al. ............... 73/864.14 |
| 4,780,833 | 10/1988 | Atake .......................... 364/509 |
| 4,896,270 | 1/1990 | Kalmakis et al. ............. 364/479 |
| 4,964,847 | 10/1990 | Prince ............................ 604/4 |
| 5,024,109 | 6/1991 | Romero et al. ............... 73/864.16 |
| 5,054,650 | 10/1991 | Price ............................... 222/1 |
| 5,059,171 | 10/1991 | Bridge et al. .................. 604/67 |
| 5,090,255 | 2/1992 | Kenney . |
| 5,182,938 | 2/1993 | Merkel ........................ 73/19.05 |
| 5,257,529 | 11/1993 | Taniguchi et al. ........... 73/54.09 |
| 5,318,359 | 6/1994 | Wakatake ..................... 366/140 |
| 5,324,480 | 6/1994 | Shumate et al. ............... 422/63 |
| 5,364,595 | 11/1994 | Smith ............................ 422/100 |
| 5,380,486 | 1/1995 | Arami ........................ 73/864.24 X |
| 5,400,664 | 3/1995 | Kio ............................. 73/863.01 |

FOREIGN PATENT DOCUMENTS

| | | |
|---|---|---|
| 0341438 | 11/1989 | European Pat. Off. . |
| 0571100 | 11/1993 | European Pat. Off. . |
| 2196963 | 2/1990 | Japan . |
| 9406020 | 3/1994 | Japan . |
| 0600419 | 3/1978 | U.S.S.R. . |
| 9318409 | 9/1993 | WIPO . |

OTHER PUBLICATIONS

"A Simple Capillary Viscometer", C. Bowlt, *Physics Education*, vol. 10, No. 2, pp. 102–103, Mar. 1975.

*Primary Examiner*—Thomas P. Noland
*Attorney, Agent, or Firm*—Mark C. Bach

[57] ABSTRACT

Embodiments described herein provide a pipetting apparatus with leak detection and a method for detecting a leak. In one embodiment, an automatic pipetting apparatus comprises a nozzle having a lower end portion through which a fluid sample is aspirated and dispensed by changes in air pressure supplied to the nozzle. A piping system operatively connects the nozzle to a pump for supplying the air pressure to the nozzle. A pressure sensor is operatively connected with the piping system for measuring internal pressure in the piping system. An XYZ robot is operatively connected with the nozzle for three-dimensionally moving the nozzle between an aspirating position of the fluid sample and a dispensing position. A leak detector is operatively connected with the pressure sensor for detecting a leak in the piping system based upon a measured result obtained by measuring the internal pressure in the piping system with the pressure sensor while the nozzle, which has aspirated a predetermined volume of the fluid sample, is being moved between the aspirating position and the dispensing position by the robot.

10 Claims, 5 Drawing Sheets

AUTOMATIC PIPETTING APPARATUS WITH LEAK DETECTION AND METHOD OF DETECTING A LEAK

BACKGROUND OF THE INVENTION

Embodiments described herein relate to an automatic pipetting apparatus provided with leak detection and a method of detecting a leak. In particular, the embodiments relate to an automatic pipetting apparatus which detects a leak in the piping system, particularly a leak caused at a joint between a nozzle base and a nozzle tip fitted to the nozzle base, by monitoring changes in internal pressure of the piping system and a method of detecting such a leak.

There are known pipetting apparatuses for pipetting fluid samples into a plurality of containers. These pipetting apparatuses are used to pipette fluid samples, such as blood extracted from a human body, into a plurality of containers. Such pipetting apparatuses are mainly employed in sample inspection sections in hospitals or the like for carrying out pretreatment pipetting operations such as a rough distribution of fluid samples to be inspected (e.g. blood plasma or blood serum) or biotechnological analysis of fluid samples, or pre-inspection pipetting operations such as radioimmunoassay (RIA) or enzyme immunoassay (EIA). Most of these pipetting apparatuses are configured into automatic pipetting apparatuses as shown in FIG. 1, in which a disposable type nozzle tip (disposable tip) as shown in FIG. 2 is used.

Figure 1:
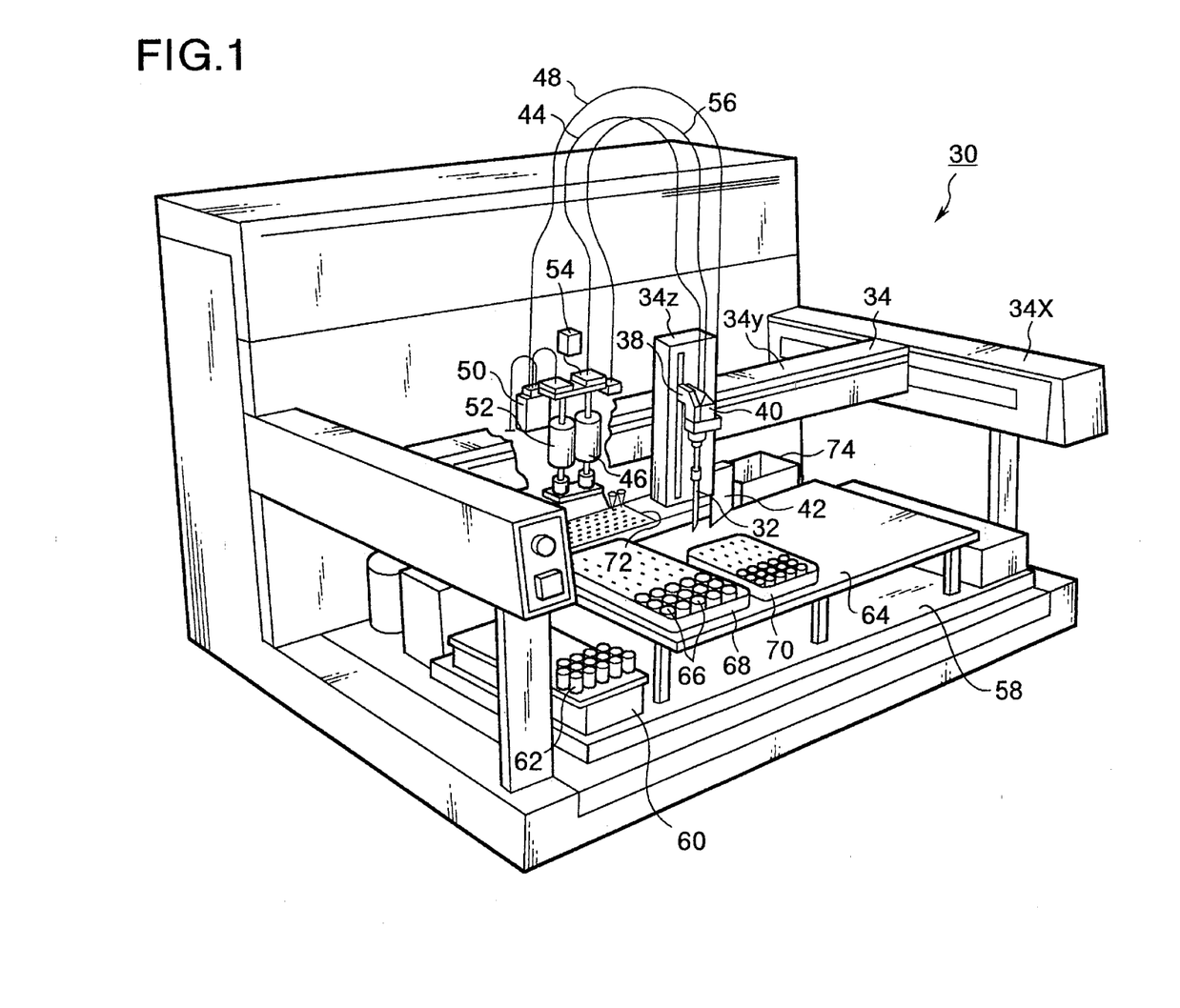
FIG. 1 is a perspective view which shows an overall structure of one embodiment of an automatic pipetting apparatus, in which a disposable tip is used.
Figure 2:
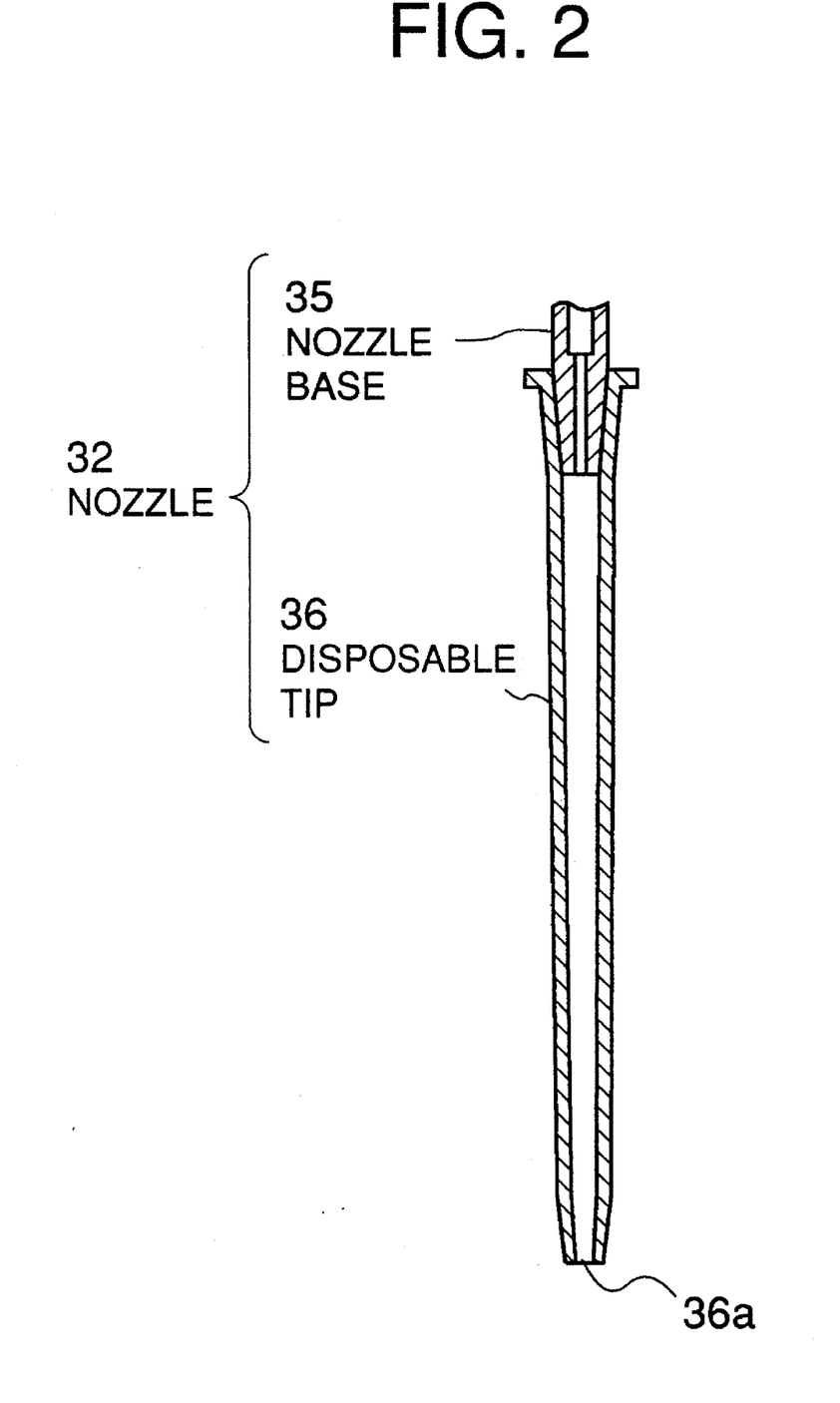
FIG. 2 is a cross-sectional view of a nozzle of the pipetting apparatus.

In the pipetting apparatus shown in FIG. 1, there is provided with a nozzle 32 for aspirating and dispensing fluid samples. The nozzle 32 is communicated with a pump through an air hose for supplying an air pressure. As clearly illustrated in FIG. 2, the nozzle 32 is constructed from a nozzle base 35 and a disposable tip 36 fitted to the nozzle base 35. In more details, at the top portion of the disposable tip 36, there is formed an opening into which the tip portion of the nozzle base 35 is tightly fitted. On the other hand, at the lower end of the disposable tip 36, there is formed a small opening 36a through which fluid samples are aspirated and dispensed. Such a disposable tip 36 is formed of a plastic material or the like, and the nozzle base 35 is formed of a metal or the like.

Now, in order for a prescribed volume of sample to be accurately pipetted, it is necessary that a proper volume of sample has been aspirated during the aspiration step. However, if there exist any air leaks (hereinafter referred to simply as "leaks or leak") in the sample aspirating passage running from the nozzle 32 to the pump 44 via the air hose, namely if there exist any leaks anywhere within the piping system, such as at the joint portions or junctions between the parts of the piping system, it will not be possible to aspirate a proper volume of sample.

Further, if such a leak exists in the piping system, there will be another problem in that any sample thus aspirated will experience a decrease in volume due to leakage of fluid sample caused by the leak in the piping system. As a result, the volume of sample to be dispensed will be insufficient, thus leading to a deterioration in the pipetting accuracy.

For these reasons stated above, in current pipetting apparatuses, a piping system thereof is examined to determine whether or not a leak exists before pipetting operations are begun. In general, the following method of examining the piping system is carried out before pipetting operations are begun. Namely, after a fluid sample has been aspirated, the nozzle is raised to place the lower end portion of the nozzle at a position above the surface of the fluid sample source. Next, with the nozzle being held motionless for a prescribed length of time, the lower end portion of the nozzle is monitored visually to determine whether or not any of the fluid sample drips from the lower end of the disposable tip. Then, a determination of the presence or absence of a leak in the piping system is made based on whether or not fluid sample drips from the disposable tip.

However, because the above method of detecting leaks is carried out only once before pipetting operations are begun, it is not possible to detect leaks occurring at the joint portion between the nozzle base 35 and the disposable tip 36 in the course of the pipetting operations. Such leaks occurring during the pipetting operations are, for example, resulted from the following cases.

Namely, there is dispersion in product quality of manufactured disposable tips because they are manufactured by molding. Therefore, if a normal quality disposable tip has been used at the time when the above described leak detecting method is carried out, no leak occurs at the joint portion between the nozzle base 35 and the disposable tip 36. However, if a poor quality disposable tip may have been used during actual pipetting operations which are subsequently carried out after the leak detecting method, such a poor disposable tip gives rise to leaks which cause the problems as described above.

Further, if foreign matter (hairs, etc.) is present at the contact portion between the nozzle base 35 and the disposable tip 36, leaks are also likely to arise at the joint portion during the pipetting operation.

Furthermore, because the disposable tip 36 is frequently replaced, the nozzle base 35 gets worn down, which also makes it easier for leaks to arise at the joint portion during the pipetting operations.

For these reasons, it is not sufficient for the pipetting apparatuses to provide with only the function that can perform the leak detection before the pipetting operations as described above, and it is desired to have another function that can detect the presence of such leaks during the pipetting operations.

In view of this problem, a leak detection method so called as a "short sample" detection method was proposed in Japanese Laid-Open Patent Application No. Hei-2-196963. Namely, in that detection method, a "Normal Sample" or "Short Sample" determination is made based on the integration value (i.e., the value corresponding to the area of a graph which shows the changes in pressure in the air hose with respect to elapsed time) calculated by integrating the pressure values of the pressure in the air hose after the aspiration of a fluid sample has been started.

However, this "short sample" detection method is only capable of detecting large leaks such as those that cause half of the prescribed volume of sample to leak out; namely, a large leak that causes the fluid sample to continuously drip out of the disposable nozzle and back into the test tube holding the fluid sample. Therefore, this method is unable to detect small leaks where sample fluid gradually flows out of the lower end opening of the disposable tip to form a drop after a proper volume of sample has been aspirated.

Another solution has been proposed in Japanese Laid-Open Patent Application No. Hei-5-249124, which discloses a pipetting apparatus and a leak detection method so called as "bubble detection method". This method is developed in view of the fact that when the volume of sample that has been aspirated into the disposable tip is insufficient due to the presence of a leak in the piping system, air is also discharged when the aspirated sample is dispensed. On the basis of this fact, in this method, insufficiency of the dispensed sample is detected by detecting such discharge of air. In more details, according to this method, just before the dispensing of the sample has been completed (i.e., after the pump has been shut off), the pressure inside the nozzle is compared with a predetermined value, and then a determination of whether or not there is any leak in the piping system is made based on whether or not the pressure inside the nozzle exceeds the predetermined value.

However, in such bubble detection method, the aspirated sample has already been dispensed into containers at the time when it is detected that there is a leak in the piping system. This means that it is not possible to immediately redo the pipetting operation when the presence of the leak is detected, because the insufficient volume of sample has already been dispensed into containers. Further, the containers which receive the insufficient volume of sample are rendered useless due to improper volume of sample. Moreover, such bubble detection method is unable to determine the presence of such a small degree of a leak that does not arise any discharge of air when the fluid sample is dispensed.

SUMMARY OF THE INVENTION

An embodiment described herein provides an automatic pipetting apparatus comprising a nozzle having a lower end portion through which a fluid sample is aspirated and dispensed by changes in air pressure supplied to the nozzle. A piping system operatively connects the nozzle to a pump for supplying the air pressure to the nozzle. A pressure sensor is operatively connected with the piping system for measuring internal pressure in the piping system. Means is operatively connected with the nozzle for three-dimensionally moving the nozzle between an aspirating position of the fluid sample and a dispensing position. Leak detecting means is operatively connected with the pressure sensor for detecting a leak in the piping system based upon a measured result obtained by measuring the internal pressure in the piping system with the pressure sensor while the nozzle, which has aspirated a predetermined volume of the fluid sample, is being moved between the aspirating position and the dispensing position by the moving means.

Another embodiment provides a method of detecting a leak in an automatic pipetting apparatus comprising a nozzle having a lower end portion through which a fluid sample is aspirated and dispensed by changes in air pressure supplied to the nozzle; a piping system operatively connecting the nozzle and a pump for supplying the air pressure to the nozzle; a pressure sensor operatively connected with the piping system for measuring internal pressure in the piping system; and means operatively connected with the nozzle for three-dimensionally moving the nozzle at least between an aspirating position and a dispensing position. In particular, the method includes aspirating a prescribed volume of the fluid sample through the nozzle at the aspirating position. The nozzle is moved from the aspirating position toward the dispensing position with the moving means. A leak in the piping system is detected based upon the internal pressure of the piping system measured by the pressure sensor while the nozzle is being moved by the moving means.

BRIEF DESCRIPTION OF ILLUSTRATED EMBODIMENTS

The embodiments described herein provide an automatic pipetting apparatus and a leak detecting method which can detect the presence of a leak in the piping system, in particular a leak that is caused at the joint portion between a nozzle base and a disposable tip, during the pipetting operations.

Also provided is an automatic pipetting apparatus and a leak detecting method which can detect any leak in the piping system in the course of the pipetting operation by changing software which controls operation of the apparatus, thereby enabling possible reduction manufacturing cost.

Generally, in accordance with the embodiments, an automatic pipetting apparatus comprises: a nozzle having a lower end portion through which a fluid sample is aspirated and dispensed using changes in an air pressure supplied to the nozzle; a piping system including the nozzle and a pump for supplying the air pressure to the nozzle; a pressure sensor for measuring the internal pressure in the piping system; an XYZ robot for three-dimensionally moving the nozzle at least from an aspirating position of the fluid sample to a dispensing position thereof; and leak detecting means for detecting any leak in the piping system based upon the measured result obtained by measuring the internal pressure in the piping system with the pressure sensor while the nozzle which has aspirated a predetermined volume of the fluid sample is being moved from the aspirating position to the dispensing position by the XYZ robot.

Accordingly, it is possible to detect the presence of a leak in the piping system, particularly at the joint portion between the nozzle base and the disposable tip, during the pipetting operation. It is preferred that the leak detecting means detects mainly a leak caused between the nozzle base and the disposable tip by monitoring changes in the internal pressure of the piping system which is caused by the leak during the pipetting operation.

It is also preferred that the leak detecting means detects the presence of the leak in the piping system by comparing a value corresponding to a pressure difference between an initial internal pressure of the piping system which is measured after the aspiration of the fluid sample and an internal pressure of the piping system which is measured while the nozzle is being moved from the aspirating position to the dispensing position, with a predetermined reference value.

Thus, it is preferred that the leak detecting means incudes: a first leak detecting means for detecting any leak in the piping system by comparing a pressure value corresponding to the pressure difference between the internal pressure of the piping system measured while the nozzle is being raised from the aspirating position and the initial internal pressure, with the reference valve; and a second leak detecting means for detecting as to whether there is any leak in the piping system by comparing a pressure value corresponding to the pressure difference between the internal pressure of the piping system measured while the nozzle is being moved horizontally to the dispensing position and the initial internal pressure, with the reference valve.

Further, it is also preferred that the XYZ robot and the pump are controlled in such a way that the fluid sample which has been aspirated into the nozzle is discharged out without executing the second leak detecting means, when the first leak detecting means detects the presence of a leak in the piping system.

Furthermore, it is also preferred that the reference value is adjustable.

Alternatively, a method of detecting leaks for use in an automatic pipetting apparatus comprises a nozzle having a lower end portion through which a fluid sample is aspirated and dispensed using changes in an air pressure supplied to the nozzle; a piping system including the nozzle and a pump for supplying the air pressure to the nozzle; a pressure sensor for measuring the internal pressure in the piping system; and a XYZ robot for three-dimensionally moving the nozzle at least from an aspirating position to a dispensing position. The method comprises the steps of: aspirating a prescribed volume of a fluid sample through the nozzle at the aspirating position; moving the nozzle from the aspirating position to the dispensing position by the XYZ robot; and detecting as to whether there is any leak in the piping system based upon the internal pressure of the piping system which is measured by the pressure sensor while the nozzle is being moved by the XYZ robot.

Further, it is also preferred that the leak detecting step further comprises the steps of: measuring an initial internal pressure of the piping system just before the aspiration of the fluid sample by the nozzle; and determining as to whether there is any leak in the piping system by obtaining a value corresponding to a pressure difference between the initial internal pressure of the piping system and the internal pressure of the piping system which is measured while the nozzle is being moved to the dispensing position by the XYZ robot, and comparing thus obtained pressure value with a prescribed reference value.

In this case, it is preferred that the leak detecting step comprises the steps of: a first leak detecting step for detecting as to whether there is any leak in the piping system by obtaining a pressure value corresponding to a pressure difference between the initial internal pressure of the piping system and the internal pressure of the piping system which is measured by the pressure sensor while the nozzle is being raised by the XYZ robot and then by comparing thus obtained pressure value with the prescribed reference value; and a second leak detecting step for detecting as to whether there is any leak in the piping system by obtaining a pressure value corresponding to a pressure difference between the initial internal pressure of the piping system and the internal pressure of the piping system which is measured by the pressure sensor while the nozzle is being moved horizontally to the dispensing position, and then by comparing thus obtained pressure value with the prescribed reference value.

Furthermore, it is also preferred that the leak detecting step further comprises the steps of: discharging the fluid sample which has been aspirated in the disposable tip without executing the second leak detecting step in the case where the presence of a leak in the piping system is detected in the first leak detecting step; and removing the disposable tip from the nozzle base and discarding it.

Other objects, structures and operations of the embodiments will be apparent when the following detailed description of a preferred embodiment is taken into account in conjunction with the accompanying drawings.

With reference to the drawings, embodiments will now be described below. In this regard, it should be noted that the same components as those in the prior art described above are indicated by the same reference numerals, and therefore the detailed description of such components are omitted in the following described.

FIG. 1 is a perspective view of an automatic pipetting apparatus 30.

The apparatus 30 is provided with a nozzle 32 for aspirating and dispensing a fluid sample. As shown in FIG. 2, the nozzle 32 is constructed from a nozzle base 35 and a disposable tip 36 formed of a plastic material. The disposable tip 36 is mounted to the nozzle base 35 by forcibly inserting the nozzle base 35 into an opening at the top end of the disposable tip 36. In the meantime, at the joint portion between the nozzle base 35 and the disposable tip 36, there is a case that a small gap is created due to the reasons stated in the above, and such a gap arises a leak of air during the pipetting operations. This construction detects mainly such a leak occurring at the joint portion during the pipetting operations.

The nozzle 32 is held by an XYZ robot 34 to enable the nozzle 32 freely movable in three dimensions. The XYZ robot 34 serves as a means for moving the nozzle 32 three-dimensionally. Namely, as shown in FIG. 1, the XYZ robot 34 is comprised of an X drive portion 34x, a Y drive portion 34y and a Z drive portion 34z. The Z drive portion 34z is provided with an elevator 38 which is freely movable up and down in the direction of the Z axis. The nozzle 32 is mounted on the elevator 38 so that it can be also moved up and down along the Z axis.

Further, this elevator 38 has a limit switch 40 which can perform the function of a jamming sensor. Namely, the limit switch 40 is constructed so as to detect an excessive force which would be exerted to the nozzle 32 when the nozzle 32 is raised over a predetermined upper position. When such an unusual movement of the nozzle 32 is detected, the limit switch 40 emits signals, and the signals are fed to a control section of the apparatus (not shown in this drawing) through a signal cable 56.

Further, an air hose 44 is provided with one end thereof being connected to the nozzle and the other end thereof being connected to a cylinder 47 of a pump 46 which produces positive and negative pressure for aspirating an dispensing a fluid sample. A diluent pipet 42 is fixedly mounted on the Z drive portion 34z for dispensing a diluent (reagent). A diluent hose 48 is provided with one end thereof connected to the diluent piper 42 and the other end thereof connected to a cylinder 52 via an electromagnetic valve 50.

In the above described construction, the passage extending from the nozzle 32 to the cylinder 47 of the pump 46 through the air hose 44 constitutes a piping system. A leak detection according to this embodiment is carried out by monitoring pressure changes in the piping system by a pressure sensor 54.

Such a pressure sensor 54 may be provided in the vicinity of the nozzle 32 which aspirates and dispenses fluid samples. However, the nozzle 32 is provided in a movable unit including the elevator 38 or the like. Therefore, if the pressure sensor 54 is mounted in the vicinity of the nozzle 32, it becomes difficult to smoothly drive the nozzle 32 since the weight of the movable unit becomes too large. On the other hand, since an internal pressure in the piping system extending from the nozzle 32 to the cylinder 47 of the pump 46 through the air hose 44 a constant anywhere in the piping system, it is not necessary to arrange such a sensor in the vicinity of the nozzle 32. Namely, for the purpose of the pressure detection, it is enough for the pressure sensor 54 to be provided anywhere in the piping system. For this reason, in the present invention, a branch passage is connected to the middle portion of the air hose 44 and the pressure sensor 54 is provided on the branch passage.

FIG. 1 further shows a test tube rack 60 being arranged on a base 58. In this connection, when a standard blood type determination is to be made, a plurality of test tubes 62 containing blood samples that have undergone a centrifugal separation treatment are held upright in the test tube rack 60. Namely, each of the test tubes 62 contains a blood sample including blood plasma and red blood cell which has been separated respectively in a top to bottom arrangement. Furthermore, a horizontal table 64 is provided on the pipetting base 58, and arranged on the horizontal table 64 is a microplate 70 and a diluent tray 68 equipped with a plurality of diluent containers 66. Formed in the microplate 70 are a plurality of wells which can hold pipetted blood plasma components or diluted red blood cell components or the like. After blood samples have been pipetted, the microplate 70 is transferred to an apparatus for determining blood type, where a coagulation determination or the like is carried out optically.

In the automatic pipetting apparatus 30 according to the present embodiment, a disposable tip is used as described above. For this reason, a tip holder 72 is provided for holding a plurality of new disposable tips, and this makes it possible to sequentially replace used tips with new tips. Furthermore, a tip disposal container 74 is provided for receiving used tips.

According to the automatic pipetting apparatus having the construction described above, the disposable tip 36 of the nozzle 32 can be freely controlled to aspirate a fluid sample such as blood serum or the like and then transfer such aspirated sample to separate containers. Naturally, fluid samples to be pipetted by the automatic pipetting apparatus described above is not limited to blood samples, and the pipetting apparatus can be used for pipetting other various fluid samples.

Figure 3:
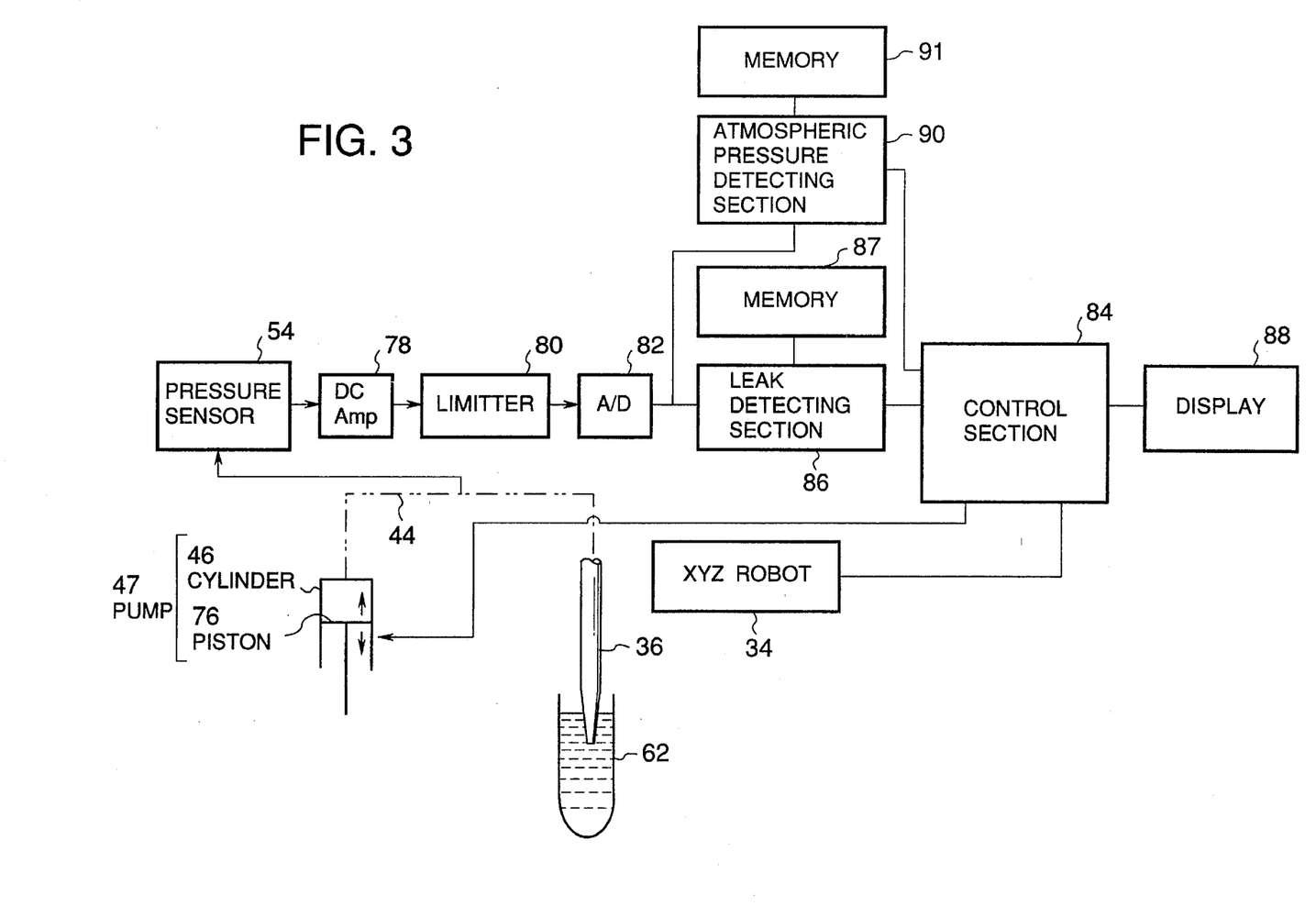
FIG. 3 is a block diagram which shows an outline of the construction of the automatic pipetting apparatus.

FIG. 3 is a block diagram showing an outline of the construction of the automatic pipetting apparatus according to the present embodiment. As shown in FIG. 3, the pump 47 is comprised of the piston 76 and the cylinder 46. In this arrangement, the volume inside the cylinder 46 is changed by moving the piston 76 up or down. Namely, by changing the volume in the cylinder 46, it is possible to selectively create either an aspirating pressure or a dispensing pressure which can be transmitted via the air hose 44 to the disposable tip 36 of the nozzle 32 to respectively aspirate or dispense a fluid sample such as a blood. In this connection, the pressure inside the air hose 44 provided between the pump 47 and the disposable tip 36, namely the pressure inside the piping system, is measured by the pressure sensor 54. The pressure sensor 54 outputs sensor signals corresponding to the measured pressures.

The sensor signals are amplified by a DC amp 78, and the sensor signals are then sent via a limiting circuit 80 to an A/D converter 82. Here, the limiting circuit 80 acts as a protection circuit to control excess input. The A/D converter 82 converts the analog sensor signals into digital signals and then sends such digital signals to a leak detecting section 86. The leak detecting section 86 detects leaks in the piping system by monitoring pressure changes inside the piping system on the basis of the digital signals. In this case, digital data which shows the pressure changes may be once stored in a memory 87, and then a determination as to whether any leak is present or not may be made based upon the stored data. An atmospheric pressure detecting section 90 is provided for measuring atmospheric pressure. Data which shows the measured atmospheric pressure is stored in a memory 91.

The control section 84 is comprised of a computer or the like and is used to control such components as the leak detecting section 86, the pump 47, the XYZ robot 34, the memory 87, the atmospheric pressure detecting section 90, and the memory 91 and the like.

The result of the leak detection made by the leak detecting section 86 is displayed in a display 88 in appropriate manners.

In the present embodiment, the pressure inside the piping system during a pipetting operation from the time aspiration of a sample is started until the time the aspirated sample is dispensed is monitored with the leak detecting section 86.

Figure 4:
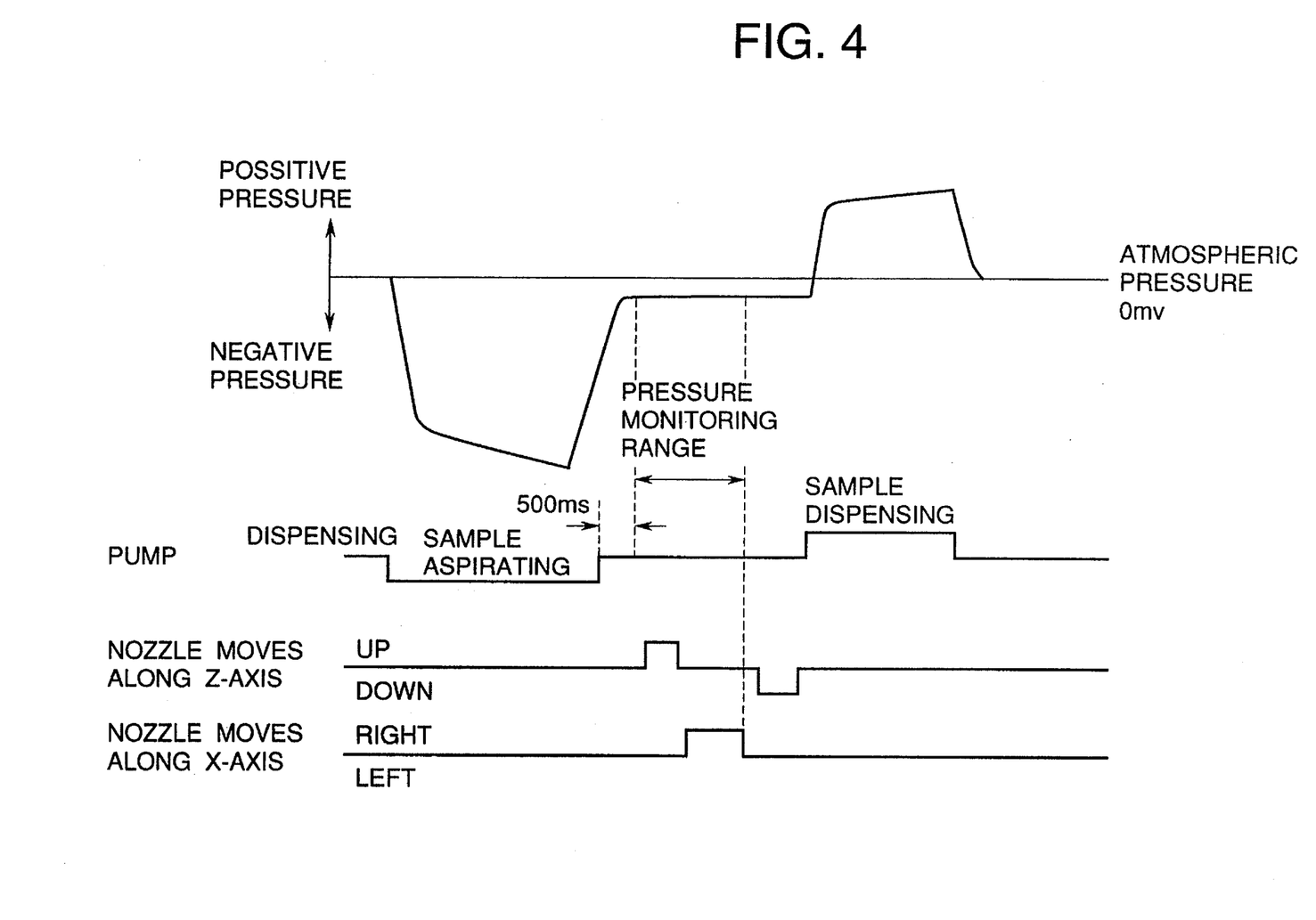
FIG. 4 is a diagram which shows changes in internal pressure of the piping system from a time of point when the sample is aspirated and a time of point when such aspirated sample is dispensed.
Figure 5:
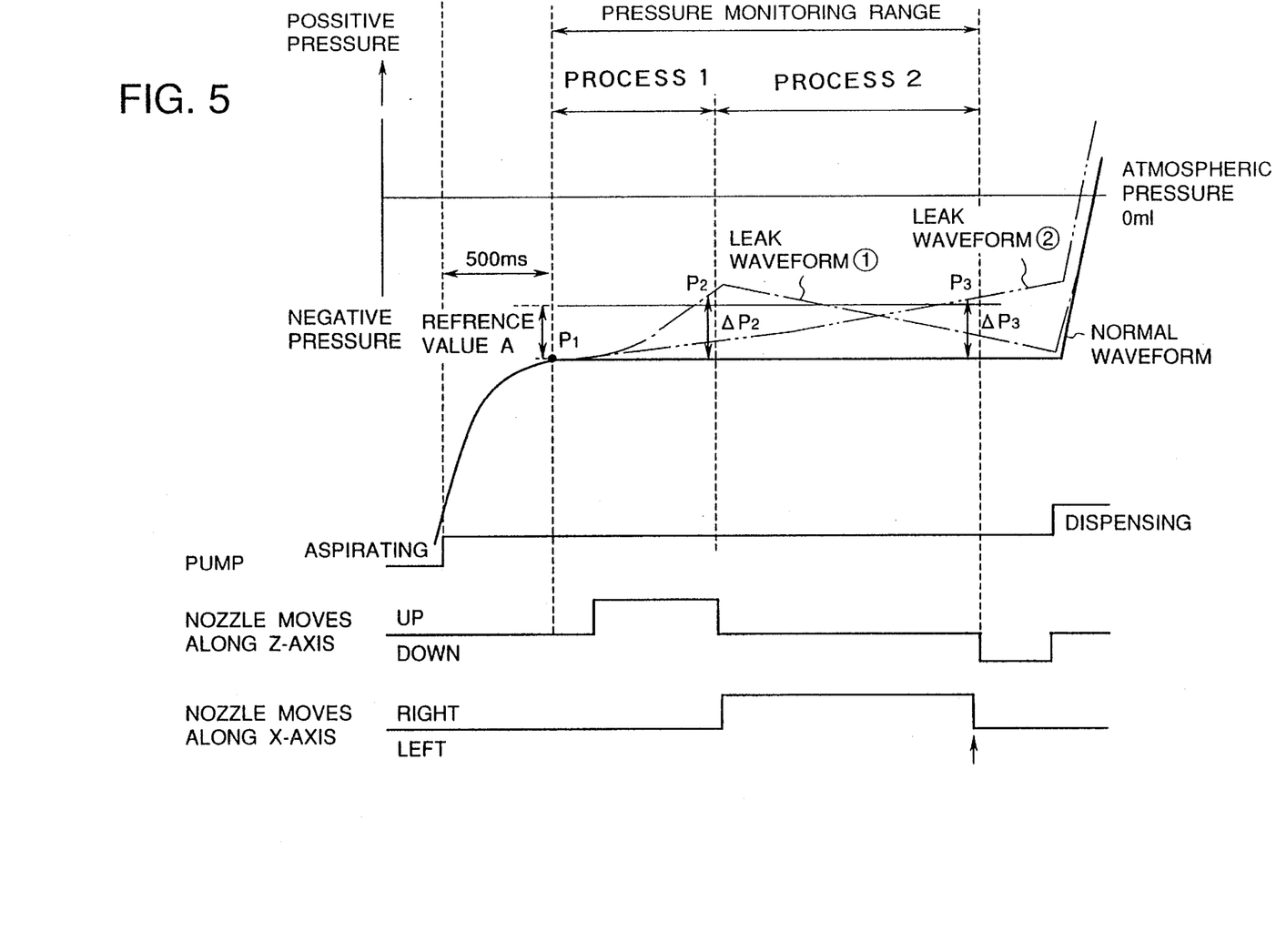
FIG. 5 is a diagram which shows changes in internal pressure of the piping system when there is a leak in the piping system of the pipetting apparatus and when there is no leak in the piping system.

Next, with reference to FIGS. 3 through 5, a description will be given for a process for detecting leaks in the piping system, particularly at the joint portion between the nozzle base 35 and the disposable tip 36, during a pipetting operation of the automatic pipetting apparatus 30. In this connection, FIG. 4 is a diagram showing the changes in the internal pressure of the piping system of the automatic pipetting apparatus 30 from the time of aspirating a fluid sample until the time of dispensing the aspirated fluid sample, and FIG. 5 is a diagram showing the changes in the internal pressure of the piping system for the case in which no leak is present and the case in which a leak is present.

For carrying out the leak detecting process, first a new disposable tip 36 is attached to the nozzle base 35 automatically.

Thereafter, the nozzle 32 is moved by the XYZ robot 34 to place the disposable tip 36 at a prescribed position above a test tube 62 containing a fluid sample and it is held at that position.

Next, the nozzle base 35 is lowered and a fluid surface detection is carried out. This fluid surface detection is performed by monitoring the internal pressure of the piping system with the pressure sensor 54. Namely, a sudden positive change in the internal pressure of the piping system occurs when the lower end of the disposable tip 36 reaches the surface of the fluid sample in the test tube 62. In this way, a determination of whether or not the lower end of the disposable tip 36 is in contact with the surface of the fluid sample in the test tube 62 can be made based on such changes in the internal pressure of the piping system.

Next, the fluid sample contained in the test tube 62 is aspirated into the disposable nozzle 36. Namely, the piston 76 of the pump 47 is retracted to increase the volume inside the cylinder 46, thereby creating a negative pressure inside the piping system which causes a prescribed volume of the fluid sample in the test tube 62 to be sucked into the disposable tip 36. At the same time, the nozzle 32 is lowered in response to the falling level of the fluid in the test tube 62 in order for the lower end of the disposable tip 36 to maintain the inserted condition into the fluid in the test tube 62 while aspiration is being carried out.

Next, as shown in FIG. 5, a prescribed time after the aspiration step has been completed, for example, 500 ms after the pump 47 has been stopped, the internal pressure $P_1$ of the piping system is measured with the pressure sensor 54 and then this pressure value $P_1$ is stored in the memory 87 as the initial internal pressure value. As for the example waiting time of 500 ms after the aspiration of the fluid sample has been completed, it is chosen for the following reasons. Namely, the internal pressure of the piping system fluctuates due to the instability existing immediately after a fluid sample has been aspirated. Accordingly, the leak detection accuracy will be adversely affected if the internal pressure of the piping system immediately after aspiration has been completed is established as the initial internal pressure value. Thus, by measuring the internal pressure of the piping system a prescribed time after a fluid sample has been aspirated and establishing this as the initial pressure value $P_1$, it is possible to avoid such instability and obtain a high leak detection accuracy.

Next, the XYZ robot 34 raises the nozzle 32 in the direction of the Z axis. Then, the XYZ robot 34 moves the nozzle 32 vertically, that is in the horizontal direction (i.e., in the directions of the X and Y axes), to place the disposable tip 36 at a sample dispensing position, for example above a microplate 70. Then, a pipetting operation is carried out by dispensing the fluid sample in the disposable tip 36 into the plurality of wells held by the microplate 70.

Hereinbelow, with reference to FIG. 5, a description of the leak detection process of the present embodiment will be given. In this connection, FIG. 5 is a graph showing the changes in the internal pressure of the piping system that occur from the time a fluid sample is aspirated until the time the aspirated sample is dispensed, with the vertical axis representing the internal pressure of the piping system and the horizontal axis representing elapsed time.

In this graph, the solid curve (hereinafter referred to as "Normal Waveform") represents a normal case in which no leak is present in the piping system, and both the single dashed curve (hereinafter referred to as "Leak Waveform 1") and the double dashed curve (hereinafter referred to as "Leak Waveform 2) represent cases in which a leak is present in the piping system. In the case represented by Leak Waveform 1, the leak in the piping system is relatively large so as to cause a drop of the fluid sample to form and appear at the lower end of the disposable tip 36 within a relatively short time span. On the other hand, in the case represented by Leak Waveform 2, the leak in the piping system is relatively small so as to cause a drop of the fluid sample to form and appear at the lower end of the disposable tip 36 within a relatively long time span.

In the present embodiment, the leak detecting section 86 detects leaks in the piping system by carrying out two leak detection processes, described below as "Process 1" and "Process 2". Namely, Process 1 is carried out from the moment after the initial pressure $P_1$ has been measured until the moment the nozzle 32 has been raised along the Z axis and then reached its original position. Process 2 is carried out while the nozzle 32 is being moved in the horizontal direction up until the moment the nozzle 32 has reached the sample dispensing position. Furthermore, $P_2$ shows the pressure of the piping system during Process 1, and $P_3$ shows the pressure of the piping system during Process 2. In this connection, when Process 1 and Process 2 are being carried out, the internal pressure of the piping system is normally monitored by measuring the internal pressure at prescribed time intervals (e.g., every 5 ms).

First, during Process 1, the pressure $P_2$ inside the piping system is monitored from the time the nozzle 32 starts to be raised above the test tube 62 holding the sample fluid until the time the nozzle 32 reaches its original position on the z-axis. Next, the pressure $P_2$ and the initial pressure $P_1$ are used to calculate $\Delta P_2$ ($P_2-P_1$). Then, $\Delta P_2$ is compared with a predetermined reference value A to make a leak determination.

In general, it is easier for a leak to occur at the time the nozzle 32 is being raised due to the effect of acceleration in addition to the weight of the fluid sample in the disposable tip 36. In this connection, as shown by the Normal Waveform of the internal pressure of the piping system in FIG. 5, in the normal case where no leak is present in the piping system, the internal pressure $P_2$ of the piping system is maintained substantially at the same pressure as the initial pressure $P_1$ while the nozzle 32 is being moved in the direction of the Z axis.

However, as shown by Leak Waveform 1, during the time the nozzle 32 is being raised, if a relatively large leak is present in the piping system, the internal pressure $P_2$ of the piping system suddenly rises toward the atmospheric pressure when a drop of the fluid sample appears at the lower end of the disposable tip 36. Then, when this drop of fluid falls from the lower end of the disposable tip 36, the internal pressure $P_2$ of the piping system decreases to return toward negative pressures due to the decrease in the amount of the fluid sample held in the disposable tip 36. While such a change in the internal pressure is happening, $\Delta P_2$ ($P_2-P_1$) is calculated at every 5 msec and compared with a prescribed reference value A to make a leak determination. If it is determined that, $\Delta P_2$ is larger than the reference value A, a "Leak" determination is made.

Now, in the case where the leak detecting section 86 makes a "Leak" determination as described above during Process 1, the XYZ robot 34 is activated to immediately lower the nozzle 32 in order to return the disposable tip 36 to the aspirating position, and then the aspirated sample is discharged back into the test tube 62. Then, after the used disposable tip 36 is discarded into the tip disposal tray 74, a new disposable tip 36 is attached to the lower end portion of the nozzle base 35 and a fluid sample is once again aspirated. Accordingly, it is possible to carry out pipetting operations without wasting any of the sample fluid.

Next, during Process 2, the internal pressure $P_3$ of the piping system is monitored at every 5 msec from the time the nozzle 32 is moved horizontally from its raised position above the test tube 62 to the dispensing position above the microplate 70. Then, after the pressure $P_3$ and the initial pressure $P_1$ are used to calculate $\Delta P_3$ ($P_3-P_1$), $\Delta P_3$ is compared with the reference value A to make a leak determination.

During Process 2, it is possible to detect a small leak in the piping system which was not detected during Process 1. Namely, Process 2 is able to detect a relatively small leak in the piping system which requires a relatively longer span of time to cause fluid to appear at the lower end of the disposable tip 36 compared with the leak that can be detected during Process 1.

Now, in the case shown by Leak Waveform 2, where air gradually leaks into the piping system due to the presence of a relatively small leak, the internal pressure $P_3$ of the piping system gradually approaches the atmospheric pressure while the nozzle 32 is being moved in the X and Y axial directions from its raised position above the test tube 62 to the dispensing position above the microplate 70. To determine the degree of such change in the internal pressure of the piping system, the internal pressure $P_3$ and the initial pressure $P_1$ are used to calculate $\Delta P_3$ ($P_3$-$P_1$). Then, $\Delta P_3$ is compared with the reference value A to make a leak determination. Namely, if $\Delta P_3$ is larger than the reference value A, a "Leak" determination is made.

In this connection, because the internal pressure of the piping system is not normal even in the case where the amount of aspirated sample that leaks out of the lower end of the disposable tip 36 is not sufficient to form a drop, there might arise a slight loss in the accuracy of the volume of sample dispensed. Namely, if the aspirated sample which has leaked out of the disposable tip 36 gets dispensed together with a prescribed volume of the sample at the time the first portion of sample is dispensed, the volume of sample actually dispensed will be slightly larger than the prescribed volume of sample intended to be dispensed. However, by having a "Leak" determination be made for such cases during Process 2, it is possible to detect even relatively small leaks before the fluid sample is dispensed. Accordingly, it is possible for an operator to be informed of a slight loss in the pipetting accuracy prior to the actual dispensing of the fluid sample being carried out.

In this connection, even if the dispensing of the fluid sample is carried out under the condition described above, the amount of fluid sample which affects the pipetting accuracy is small in comparison to the case where an actual drop of fluid leaks out of the disposable tip 36. Accordingly, it is possible to continue the pipetting operation if the required pipetting accuracy allows to do so. On the other hand, if the required pipetting accuracy does not allow to do so, it is possible to stop and redo the pipetting operation from the beginning with a new disposable tip. In this way, it becomes possible to improve operational efficiency in the pipetting operation even if presence of a leak is detected.

Now, in the case where $\Delta P_2$ is smaller than the reference value A during Process 1 and $\Delta P_3$ is smaller than the reference value A during Process 2, a "Normal" determination is made and the pipetting operations are continued.

Furthermore, in the case where a "Leak" determination was made either during Process 1 or Process 2, this information can be displayed by a display 88 which is constituted from a monitor, printer or the like in order to inform the operator that a leak has been detected. Moreover, an alarm device may be employed to announce the detection of a leak to the operator. In this way, it is possible to precisely report the state of the leak to the operator, and this makes it possible to vastly improve the pipetting accuracy.

In this connection, the state of any leaks in the piping system will depend on factors such as the viscosity and surface tension of the fluid being aspirated, with viscosity and surface tension being different from each other dependent on the type of fluid being aspirated and the temperature thereof. Accordingly, the reference values A for determining the degree of a leak may be changed to take such factors into account. For example, by taking into account the type of fluid, the capacity of disposable tip, the diameter of the lower end opening of the disposable tip, the required pipetting accuracy and the like, it is possible to set an effective reference value A so as to suit such conditions.

Furthermore, because the degree of acceptable leakage depends on the required pipetting accuracy, the pipetting accuracy is taken into account when deciding the degree of acceptable leakage. For example, by making the reference value A extremely small, it is possible to detect relatively small leaks such as those which result in the leakage of only a small amount of fluid from the lower end of the disposable tip, and this makes it possible to improve the pipetting accuracy. On the other hand, in the case where a relatively low pipetting accuracy is required, by making the reference value A large, the disposable tip need not be changed except when necessary, thereby reducing consumption of disposable tips.

Moreover, even though it is possible for the reference value A to have different values for Process 1 and Process 2, it is preferred that the reference value A be the same for Process 1 and Process 2, as was described in the present embodiment. In this way, operations can be simplified because the setting of the reference value A is made easy and no switching of values for the reference value A is required when going from Process 1 to Process 2.

In connection with the above described embodiment of the present invention, it should be noted that the output from the pressure sensor 54 is voltage, and the leak detection in the leak detecting section 86 is carried out based upon the data corresponding to the voltage.

Furthermore, the characteristics of this pipetting apparatus can be easily applied to other pipetting apparatuses by installing an appropriate software which can execute the above process, if they have a pressure sensor which can perform a fluid surface detection as described above. Therefore, this method is valuable in economical viewpoint.

Finally, it should be noted that the above described embodiments is only one example of the described properties of the automatic pipetting apparatus.

What is claimed is:

1. An automatic pipetting apparatus, comprising:
   (a) a nozzle having a lower end portion through which a fluid sample is aspirated and dispensed by changes in air pressure supplied to said nozzle;
   (b) a piping system operatively connecting said nozzle to a pump for supplying the air pressure to said nozzle;
   (c) a pressure sensor operatively connected with the piping system for measuring internal pressure in said piping system;
   (d) means for three-dimensionally moving said nozzle at least between an aspirating position of the fluid sample and a dispensing position; and
   (e) leak detecting means operatively connected with the pressure sensor for detecting a leak in said piping system based upon a measured result obtained by measuring the internal pressure in said piping system with said pressure sensor while said nozzle, which has aspirated a predetermined volume of the fluid sample, is being moved between the aspirating position and the dispensing position by said moving means.

2. The automatic pipetting apparatus as claimed in claim 1, wherein said nozzle has a nozzle base and a disposable tip fitted to said nozzle base, said leak detecting means constructed to detect a leak adjacent a joint portion between said nozzle base and said disposable tip by monitoring changes in the internal pressure of said piping system caused by said leak during pipetting operation.

3. The automatic pipetting apparatus as claimed in claim 1, wherein said leak detecting means is constructed for detecting presence of the leak in said piping system by comparing a value, corresponding to a pressure difference between an initial internal pressure of the piping system which is measured after aspiration of the fluid sample and an internal pressure of the piping system which is measured while said nozzle is being moved from the aspirating position to the dispensing position, with a predetermined reference value.

4. The automatic pipetting apparatus as claimed in claim 3, wherein said moving means is constructed to raise the nozzle substantially vertically from the aspirating position after aspiration of the fluid sample and to move the nozzle substantially horizontally to the sample dispensing position, wherein said leak detecting means incudes:

(i) a first leak detector for detecting a leak in said piping system by comparing a pressure value, corresponding to a pressure difference between the internal pressure of said piping system measured while said nozzle is being raised from the aspirating position and said initial internal pressure, with said reference value; and (ii) a second leak detector for detecting a leak in said piping system by comparing a pressure value, corresponding to a pressure difference between the internal pressure of said piping system measured while said nozzle is being moved substantially horizontally toward the dispensing position and said initial internal pressure, with said reference value.

5. The automatic pipetting apparatus as claimed in claim 4, further comprising:

(f) means for controlling said moving means and said pump such that the fluid sample which has been aspirated into the nozzle is discharged without executing said second leak detector when said first leak detector detects presence of a leak in said piping system.

6. The automatic pipetting apparatus as claimed in claim 3, wherein said reference value is adjustable.

7. A method of detecting a leak in an automatic pipetting apparatus comprising a nozzle having a lower end portion through which a fluid sample is aspirated and dispensed by changes in air pressure supplied to said nozzle; a piping system operatively connecting said nozzle and a pump for supplying the air pressure to said nozzle; a pressure sensor operatively connected with the piping system for measuring internal pressure in said piping system; and means operatively connected with the nozzle for three-dimensionally moving said nozzle at least between an aspirating position and a dispensing position, wherein said detecting method comprises the steps of:

(a) aspirating a prescribed volume of the fluid sample through said nozzle at the aspirating position;

(b) moving said nozzle from the aspirating position toward the dispensing position with said moving means; and (c) detecting a leak in said piping system based upon the internal pressure of the piping system measured by said pressure sensor while said nozzle is being moved by said moving means.

8. The method of detecting a leak in an automatic pipetting apparatus as claimed in claim 7, wherein said leak detecting step (c) further comprises the steps of:

(i) measuring an initial internal pressure of said piping system just before aspiration of the fluid sample by said nozzle; and (ii) determining a leak in said piping system by obtaining a value corresponding to a pressure difference between the initial internal pressure of the piping system and the internal pressure of the piping system which is measured while said nozzle is being moved toward the dispensing position by said moving means, and comparing thus obtained pressure value with a prescribed reference value.

9. The method of detecting a leak in an automatic pipetting apparatus as claimed in claim 8, wherein said leak detecting step (c) comprises the steps of:

(iii) a first leak detecting step for detecting a leak in said piping system by obtaining a pressure value corresponding to a pressure difference between the initial internal pressure of said piping system and the internal pressure of said piping system measured by said pressure sensor while said nozzle is being raised from the aspirating position by said moving means and then by comparing thus obtained pressure value with the reference value; and (iv) a second leak detecting step for detecting a leak in said piping system by obtaining a pressure value corresponding to a pressure difference between the initial internal pressure of said piping system and the internal pressure of said piping system which is measured by said pressure sensor while said nozzle is being moved substantially horizontally toward the dispensing position by said moving means, and then by comparing thus obtained pressure value with the prescribed reference value.

10. The method of detecting a leak in an automatic pipetting apparatus as claimed in claim 9, wherein said nozzle include a nozzle base and a disposable tip fitted to said nozzle base, wherein said leak detecting step further comprising the steps of:

(v) discharging the fluid sample from said disposable tip without executing said second leak detecting step when the first leak detecting step detects presence of a leak in said piping system; and (vi) removing said disposable tip from said nozzle base and discarding it.

* * * * *